United States Patent
Duggan et al.

[11] Patent Number: 6,124,594
[45] Date of Patent: Sep. 26, 2000

[54] METHOD AND APPARATUS FOR DETECTING CONTACT LENSES

[75] Inventors: Robert G. Duggan, Piltown; Joseph Patrick Dowling, Waterford, both of Ireland

[73] Assignee: Bausch & Lomb Incorporated, Rochester, N.Y.

[21] Appl. No.: 09/151,560

[22] Filed: Sep. 11, 1998

[51] Int. Cl.[7] .................................................. G01B 9/00
[52] U.S. Cl. .................................. 250/341.8; 250/339.1; 250/339.06
[58] Field of Search ............................ 250/339.06, 339.1, 250/341.8

[56] References Cited

U.S. PATENT DOCUMENTS

| | | | |
|---|---|---|---|
| 5,049,216 | 9/1991 | Shead et al. ............................ | 156/64 |
| 5,500,732 | 3/1996 | Ebel et al. ............................... | 356/124 |
| 5,526,119 | 6/1996 | Blit et al. ................................ | 356/402 |
| 5,568,715 | 10/1996 | Ebel et al. ................................ | 53/54 |
| 5,722,536 | 3/1998 | Pierce et al. ........................... | 206/5.1 |
| 5,970,983 | 10/1999 | Karni et al. ............................ | 128/898 |

FOREIGN PATENT DOCUMENTS

| | | |
|---|---|---|
| 070252 | 1/1983 | European Pat. Off. . |
| 0 686 459 A2 | 12/1995 | European Pat. Off. . |
| 0 691 273 A1 | 1/1996 | European Pat. Off. . |
| 84/02398 | 6/1984 | WIPO . |
| 95/04264 | 2/1995 | WIPO . |

*Primary Examiner*—Constantine Hannaher
*Assistant Examiner*—Otilia Gabor
*Attorney, Agent, or Firm*—John E. Thomas

[57] ABSTRACT

A method and apparatus for confirming the presence of a contact lens in its intended package employs an infrared detection system that is able to detect the presence or absence of a contact lens in the package.

12 Claims, 1 Drawing Sheet

METHOD AND APPARATUS FOR DETECTING CONTACT LENSES

BACKGROUND OF THE INVENTION

This invention relates to a method and apparatus for confirming the presence of a contact lens, especially for confirming the presence of a lens in its package prior to completing the packaging operation.

A conventional manner of packaging contact lenses is in so-called "blister packages". Such packages include a recess designed to hold an individual lens, usually in a saline solution in the case of soft hydrogel lenses. The packages are then enclosed and sealed with a lidstock, the lidstock conventionally being a metallic laminate such as a laminate including an aluminum layer, that can withstand post-packaging heat sterilization conditions. Frequently, multiple blister packages of contact lenses are then enclosed in a secondary carton which conventionally has the form of a paperboard box.

Automation offers increased speed and less human handling in packaging products such as contact lenses in blister packages. However, a drawback is that errors in automated packaging operations may more easily go undetected. The present invention provides a method and apparatus that can confirm that a contact lens has been placed in its package as intended.

SUMMARY OF THE INVENTION

The invention provides a method for confirming the presence of a contact lens in a package. The method involves aligning the package with an infrared detection system that detects the presence or absence of a contact lens in the package. The invention further relates to an apparatus for carrying out the method.

BRIEF DESCRIPTION OF THE DRAWING FIGURES

DETAILED DESCRIPTION OF PREFERRED EMBODIMENTS

Figure 1:
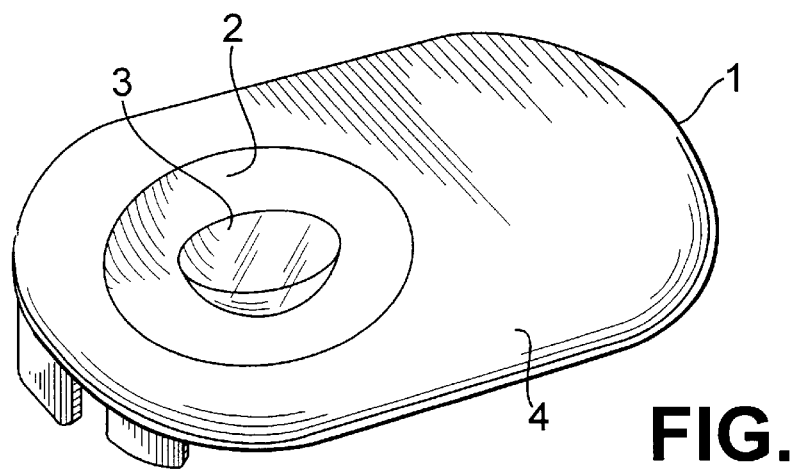
FIG. 1 is a perspective view of a contact lens blister package.

FIG. 1 illustrates a blister package for contact lenses. As seen in FIG. 1, blister package 1 includes recess 2 for holding an individual contact lens 3. Recess 2 terminates at surface 4, and typically a metallic lidstock is sealed to surface 4 so as to sealingly encase recess 2 and enclose package 1. It is conventional for such packages to contain saline solution sealed in recess 2 along with the lens.

An occasional problem in manufacturing contact lenses is that a lens may be missing from the blister package, whereupon the package is sealed without noticing the missing lens. The absence of a lens is more likely to go unnoticed in an automated or semi-automated manufacturing process where an operator is not manually placing a lens in each package immediately before the sealing operation.

Figure 2:
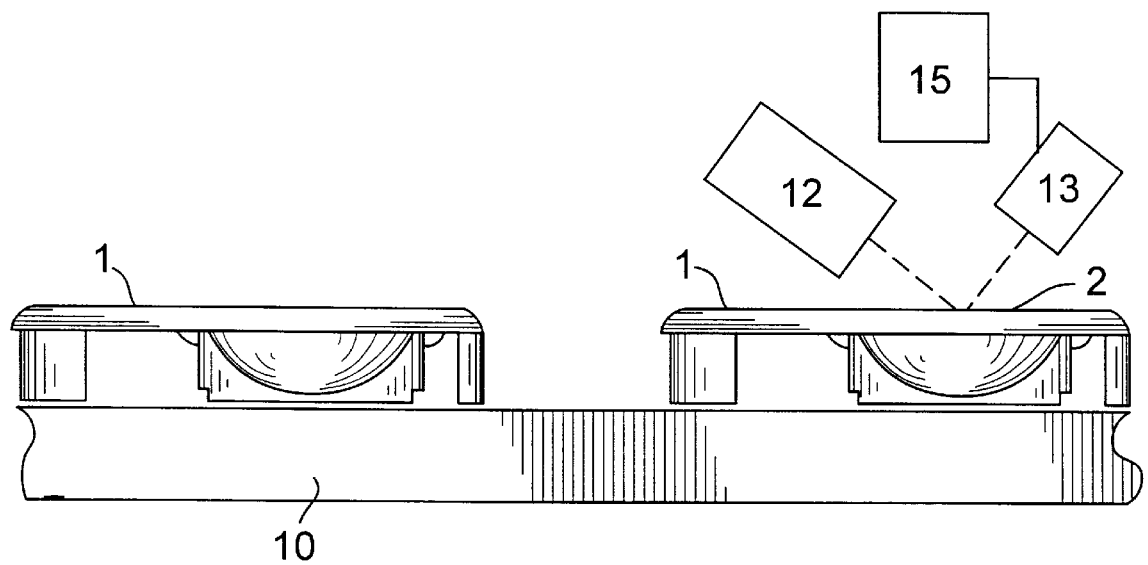
FIG. 2 is a side perspective view of the blister package and an apparatus according to an embodiment of the invention.

FIG. 2 illustrates schematically an apparatus for confirming the presence of a contact lens in package 1. The apparatus includes stepped conveyor 10 for transporting packages 1. Positioned along the conveyor are at least one infrared radiation source 12 and a corresponding infrared detector 13. Detector 13 is connected to controller 15 programmed in a manner that if the detector does not render a predetermined reading (i.e., does not detect the presence of a contact lens in the package), corrective action can be taken. For example, an alarm can be sounded to alert an operator, or the package missing the lens can be removed automatically from the queue.

According to a first embodiment, the operation of the apparatus is based on principles of infrared analysis. Organic molecules, in general, contain interatomic valence bonds which exhibit characteristic resonance frequencies in the IR range. For example, soft hydrogel contact lenses are conventionally formed of polymers based on at least one monomer having (meth)acrylate functionality. The C=O bond in such (meth)acrylates strongly absorbs IR radiation at a wavenumber of about 1725 cm$^{-1}$. In contrast, contact lens blister packages are conventionally made of a material such as polypropylene, which does not include any C=O bond.

Accordingly, the IR radiation source 12 projects IR radiation towards recess 2 of package 1, recess 2 intending to include a contact lens. Detector 13 detects a portion of infrared radiation reflected from recess 2. Controller 15, connected to detector 13, performs Fourier Transform Infrared (FTIR) spectroscopy analysis of the radiation received at the detector to confirm the presence or absence of absorption of IR radiation at wavenumbers in the vicinity of 1725 cm$^{-1}$. Detection of absorption of IR radiation in this range confirms that a contact lens is presence; lack of absorption in this range confirms that no contact lens is presence.

As mentioned, contact lenses are conventionally packaged in saline solution. Since such solutions do not typically include any organic molecules having the C=O bond, the IR detection can be performed after saline solution has been added to the blister package recess.

According to a second embodiment, the operation of the apparatus is based on IR moisture detection. Referring again to FIG. 2, the apparatus again includes conveyor 10 for transporting packages 1. Positioned along conveyor 10 are at least one infrared radiation source 12 and a corresponding detector having the form of an infrared moisture sensor, such that infrared moisture sensor 13 detects a portion of infrared radiation reflected from recess 2 of package 1.

Soft hydrated, hydrogel contact lenses typically contain at least 30 weight percent water. Accordingly, moisture sensor 13 detects the moisture content from the reflected beam. Detection of a moisture level corresponding to the hydrated contact lens confirms that a contact lens is presence; failure to detect this moisture level confirms that no contact lens is presence. For example, in the case where detection is performed before filling the recess with water, if a hydrated lens is missing, the moisture detector will indicate a moisture level at or near 0 percent rather than a moisture level corresponding to that of the hydrated contact lens. It may also possible to perform detection after filling the recess with saline solution, in which case, if a lens is missing the moisture detector will indicate a moisture level near 100 percent, well above that of a hydrated contact lens, although it is preferred to perform the IR detection prior to filling the blister package recess with saline solution.

Many other modifications and variations of the present invention will be evident to the skilled practitioner. As one example, several IR sources and corresponding detectors may be aligned in series, so that several packages, each package aligned with an IR sources and a detector, can be examined simultaneously. As another example, the apparatus may be modified such that the detector is positioned below the package, wherein IR radiation is transmitted from the IR source through the package to the detector. As a further example, the invention is applicable for blister packages having configurations other than shown in the figures. It is therefore understood that, within the scope of the claims, the present invention is not limited to the described preferred embodiments and can be practiced other than as herein specifically described.

We claim:

1. A method for confirming the presence of a contact lens in a package comprising aligning a package for holding a contact lens with an infrared detection system, wherein the system detects the presence or absence of a contact lens in the package, and wherein the system comprises an infrared radiation source directed to the package, and a receiver to receive at least a portion of infrared radiation directed from the package to the receiver.

2. The method of claim 1, wherein infrared radiation is directed through the package to the receiver.

3. The method of claim 1, wherein infrared radiation is reflected from the package to the receiver.

4. The method of claim 1, wherein the package comprises a recess designed to hold an individual contact lens.

5. The method of claim 4, wherein the system detects the presence or absence of a hydrogel contact lens.

6. The method of claim 5, wherein the package recess includes saline solution.

7. An apparatus comprising:

a conveyor that transports packages for containing contact lenses, and an infrared detection system arranged along said conveyor that detects the presence or absence of a contact lens in the package, wherein the infrared detection system comprises an infrared radiation source directed to the package, and a receiver to receive at least a portion of infrared radiation directed from the package to the receiver.

8. The apparatus of claim 7, wherein infrared radiation is directed through the package to the receiver.

9. The apparatus of claim 7, wherein infrared radiation is reflected from the package to the receiver.

10. The apparatus of claim 7, wherein the package comprises a recess designed to hold an individual contact lens.

11. The method of claim 10, wherein the system detects the presence or absence of a hydrogel contact lens.

12. The method of claim 11, wherein the package recess includes saline solution.

* * * * *